United States Patent [19]
Rau et al.

[11] Patent Number: 6,024,722
[45] Date of Patent: Feb. 15, 2000

[54] THERMOPLASTIC POLYIMIDE BALLOON CATHETER CONSTRUCTION

[75] Inventors: Bruce H. Rau, Clearwater; Susan M. Shoemaker, Elk River; Paul J. Buscemi, Long Lake, all of Minn.

[73] Assignee: SciMed Life Systems, Inc., Maple Grove, Minn.

[21] Appl. No.: 08/817,165

[22] PCT Filed: Dec. 27, 1994

[86] PCT No.: PCT/US94/14970

§ 371 Date: Oct. 2, 1997

§ 102(e) Date: Oct. 2, 1997

[87] PCT Pub. No.: WO95/18647

PCT Pub. Date: Jul. 13, 1995

Related U.S. Application Data

[63] Continuation-in-part of application No. 08/177,911, Jan. 6, 1994.

[51] Int. Cl.[7] .................................................. A61M 29/00
[52] U.S. Cl. ........................... 604/96; 604/524; 606/194
[58] Field of Search ............................. 604/96, 101, 264, 604/280, 524–527; 606/192, 194

[56] References Cited

U.S. PATENT DOCUMENTS

| | | |
|---|---|---|
| 32,983 | 7/1861 | Levy . |
| 33,561 | 3/1861 | Levy . |
| 4,238,538 | 12/1980 | Manwiller . |
| 4,413,989 | 11/1983 | Schjeldahl et al. . |
| 4,456,000 | 6/1984 | Schjeldahl et al. . |
| 4,490,421 | 12/1984 | Lavy . |
| 4,880,584 | 11/1989 | Jones et al. ............................. 264/135 |
| 4,952,357 | 8/1990 | Euteneuer . |
| 4,954,610 | 9/1990 | Chen, Sr. et al. . |
| 5,032,113 | 7/1991 | Burns . |

(List continued on next page.)

FOREIGN PATENT DOCUMENTS

| | | |
|---|---|---|
| 0 274 411 A2 | 7/1988 | European Pat. Off. . |
| 0 380 102 A1 | 8/1990 | European Pat. Off. . |
| 0 391 633 A2 | 10/1990 | European Pat. Off. . |
| 0 420 486 A1 | 4/1991 | European Pat. Off. . |
| 0 457 456 A1 | 11/1991 | European Pat. Off. . |
| 0 541 055 A1 | 5/1993 | European Pat. Off. . |
| 40 25 346 A1 | 2/1992 | Germany . |
| WO 89/08471 | 9/1989 | WIPO . |
| WO 92/08512 | 5/1992 | WIPO . |
| WO 93/20881 | 10/1993 | WIPO . |

OTHER PUBLICATIONS

T.L. St. Clair and H.D. Burks, NASA Langley Research Center, Hampton, Virginia; Thermoplastic, Melt–processsable Polyimides, Conference Publication 2334, pp. 337–355.

NASA Conf. Pub. #2334, (1984) pp. 337–355, Thermoplastic/Melt–Processable Polyimides, T.L. St. Clair and H.D. Burks.

*Modern Plastics International*, Jun. 1990, p. 71, TP polyimide is easy to process.

*Modern Plastics International*, Apr. 1992, pp. 19–20, Direct–form materials now are melt–processable as well, Patrick A. Toensmeier.

*Thermoset Extrusions New Answers to Old Problems*, By Ted Jex, Jan. 1977.

N.A. Androva et al. *Polyimides, A New Class of Heat–Resistant Polymers*, pp. 4–13, Israel Program for Scientific Translations, 1969.

*Primary Examiner*—Corrine McDermott
*Attorney, Agent, or Firm*—Vidas, Arrett & Steinnkraus

[57] ABSTRACT

The present invention discloses the incorporation of thermoplastic polyimide into various parts of balloon catheters such as catheter shafts and balloons. Such catheter constructions may be integral or unitary in which the shaft of a portion thereof and balloon are manufactured as a single unit or the construction may be comprised of a separate shaft to which a balloon is attached as by adhesive or other bonding.

11 Claims, 4 Drawing Sheets

U.S. PATENT DOCUMENTS

| | | | |
|---|---|---|---|
| 5,047,045 | 9/1991 | Arney et al. | 606/194 |
| 5,069,848 | 12/1991 | Saruwatari et al. | |
| 5,087,394 | 2/1992 | Keith | |
| 5,100,381 | 3/1992 | Burns | |
| 5,163,989 | 11/1992 | Campbell et al. | |
| 5,169,397 | 12/1992 | Sakashita et al. | |
| 5,176,661 | 1/1993 | Evard et al. | |
| 5,176,698 | 1/1993 | Burns et al. | |
| 5,180,368 | 1/1993 | Garrison | |
| 5,207,700 | 5/1993 | Euteneuer | |
| 5,248,305 | 9/1993 | Zdrahala | |
| 5,328,472 | 7/1994 | Steinke et al. | 604/12 |
| 5,447,497 | 9/1995 | Sogard et al. | 604/101 |

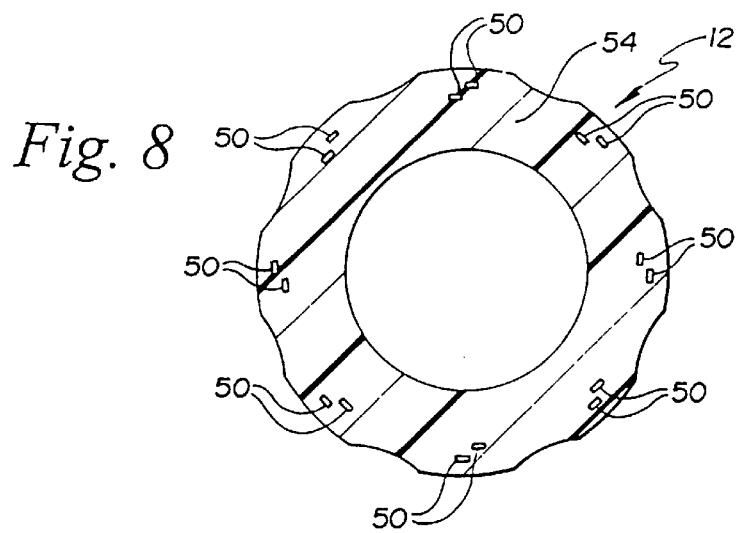
Fig. 8
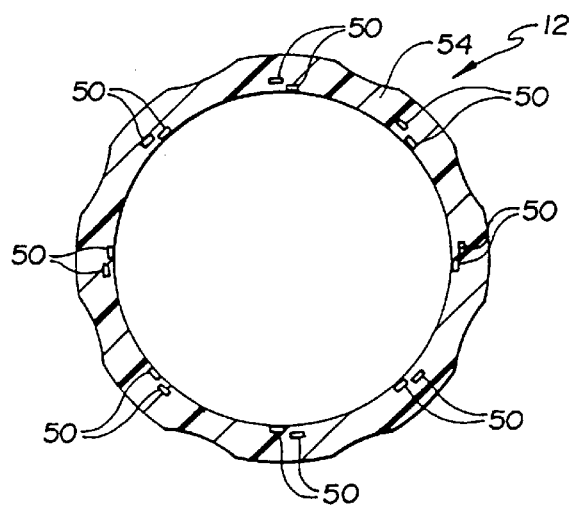
Fig. 9
Fig. 10
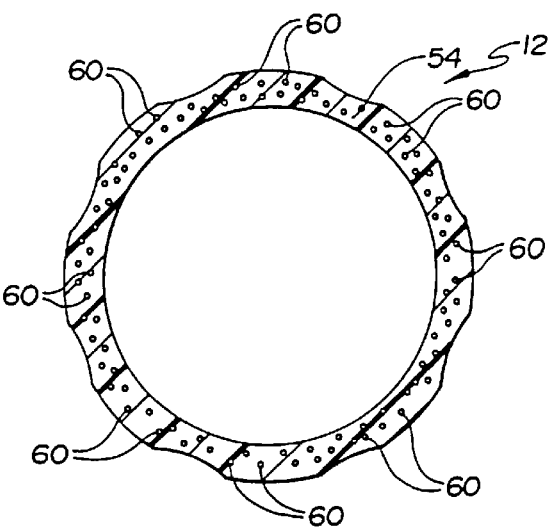

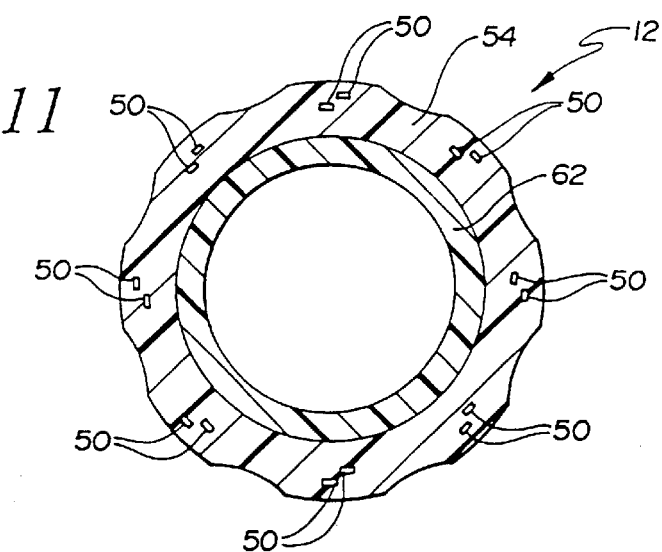
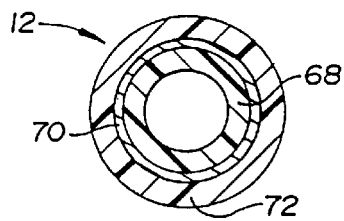
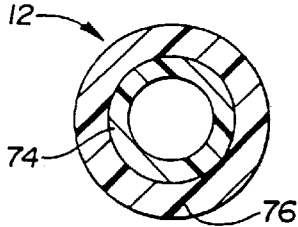
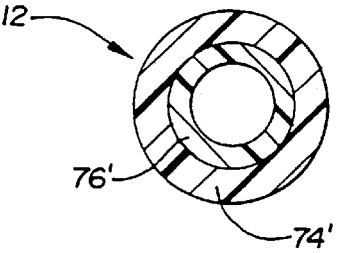
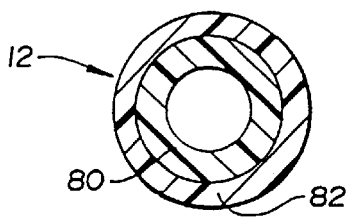
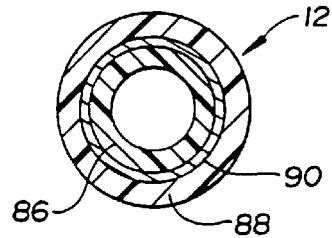
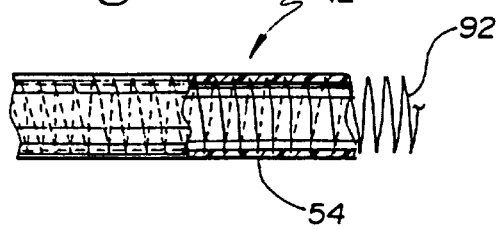

THERMOPLASTIC POLYIMIDE BALLOON CATHETER CONSTRUCTION

CROSS REFERENCE TO RELATED APPLICATIONS

This application is a continuation in part of U.S. patent application Ser. No. 08/177,911 filed Jan. 6, 1994, the disclosure of which is incorporated herein by reference.

BACKGROUND OF THE INVENTION

This invention relates to dilation balloon catheters, particularly those used in angioplasty. More specifically, it relates to the balloons on such catheters and to some extent to the catheter shaft as well. Angioplasty relates to opening of stenoses in the vascular system usually by means of a catheter having a balloon at its distal end. Such catheters may be single or multiple lumen, may be over-the-wire or non-over-the-wire. Very similar catheters may be used for placing stents. All such catheters are referred to herein collectively as "balloon catheters". The invention described herein could also be utilized in the production and manufacture of guide catheters or infusion catheters.

It is possible to make balloons from a variety of materials that are generally of the thermoplastic polymeric type. Such materials may include: polyethylenes and ionomers, ethylene-butylene-styrene block copolymers blended with low molecular weight polystyrene and, optionally, polypropylene, and similar compositions substituting butadiene or isoprene in place of the ethylene and butylene; poly(vinyl chloride); polyurethanes; copolyesters; thermoplastic rubbers; siliconepolycarbonate copolymers; and ethylene-vinyl acetate copolymers.

One material of choice for such catheters has been thermoset polyimide, primarily because of its high strength and flexibility in small diameter with very thin walls. Being thermoset, the polyimide used heretofore has involved complicated manufacturing procedures due to the fact that it is insoluble and "intractable" i.e., not meltable. For example, in forming catheter shafts, it has been necessary to build up the shaft with multiple layers of polyimide on a substrate which is subsequently dissolved away. This has also been necessary in making the catheter balloon in which multiple layers of thermoset polyimide were layered onto a form, of glass for example, which was later etched away leaving a polyimide balloon.

This type of polyimide is a heterochain polymer typically made of two base monomers, a diamine and a dianhydride (e.g. para-aminoaniline and pyromellitic dianhydride). Such polyimide is typically formed by two step reaction like the following example. First, a polyamide is formed from the monomers. The reaction proceeds at about 25° C. and the product is soluble and stable in very polar solvents. Second, the polyamide is condensed to polyimide at about 120° C. Further description of polyimides and their preparation can be found in Androva et al. *Polyimide, A New Class of Hear-Resistant Polymers*, pp. 4–13 (1969).

As already indicated other plastics have been used in catheter construction for shafts and balloons in which the plastic has been of the thermoplastic type. For example, polyethylene terephthalate (PET) has been used to make the balloons. Thermoplastic materials lend themselves to simpler manufacturing techniques, such as extrusion in forming shafts and blow molding in forming the balloons than do the aforementioned thermoset polyimide materials due to the fact that they are soluble and meltable. However, the art has failed to recognize that thermoplastic polyimide is available for balloon catheter construction.

Although many of the procedures employing balloon catheters are still in the experimental stage in the United States, there is a considerable amount of art available on the formation and use of balloon catheters. Illustrations of such art are: U.S. Pat. Nos. 4,952,357 to Euteneuer; 4,413,989 and 4,456,000 to Schjeldahl et al. and 4,490,421 as well as Reissue Patent Nos. 32,983 and 33,561 to Levy.

The Euteneuer patent relates to the prior art polyimide catheter/balloon construction. The Schjeldahl patents, incorporated herein by reference, pertain to catheter assemblies or attachments. These patents disclose expanders (balloons) formed from a thin, flexible, inelastic, high tensile strength, biaxially oriented, synthetic plastic material. The Levy patents, which issued several years after the Schjeldahl patents, sought to provide balloons exhibiting physical properties superior to those exhibited by prior art balloons. The specific qualities Levy emphasized were toughness, flexibility and tensile strength. Levy teaches that a high tensile strength balloon can only be formed from a high intrinsic viscosity polymer, specifically, high molecular weight polyethylene terephthalate.

High tensile strengths are important in angioplasty balloons because they allow for the use of high pressure in a balloon having a relatively small wall thickness. High pressure is often needed to treat some forms of stenosis. Small wall thicknesses enable the deflated balloon to remain narrow, making it easier to advance the balloon through the arterial system.

SUMMARY OF THE INVENTION

It is the primary purpose of this invention to apply thermoplastic polyimide to the art of balloon catheter construction, i.e., to catheter shafts and balloons. It is another purpose of this invention to apply thermoplastic polyimide to the art of guide catheter construction and infusion catheter construction. Such catheter construction may be either integral or unitary in which the shaft or a portion thereof and balloon are manufactured as a single unit or the construction may be comprised of a separate shaft to which a balloon is attached, as by adhesive or other bonding.

BRIEF DESCRIPTION OF THE DRAWINGS

A detailed description of the invention is hereafter described with specific reference being made to the drawings in which:

FIG. 8 is a cross-sectional view of a shaft according to the present invention, wherein the shaft has a reinforcement material embedded in the outermost diameter of the polyimide substrate;

FIG. 9 is a cross-sectional view of a shaft according to the present invention, wherein the shaft has a reinforcement material at its innermost diameter with polyimide coating the reinforcement structure;

FIG. 10 is a cross-sectional view of a shaft according to the present invention, wherein the shaft is formed from a blend of polyimide and a reinforcing material;

FIG. 11 is a cross-sectional view of a shaft according to the present invention, wherein the shaft is formed of a fluoropolymer at the inner diameter, a layer of polyimide surrounding the fluoropolymer layer and a reinforcement material bonded to or embedded in the polyimide layer;

FIG. 12 is a cross-sectional view of a shaft according to the present invention, wherein said shaft is formed of a polyimide inner layer, an intermediate reinforcing material and an outer polyimide layer;

FIG. 13 is a cross-sectional view of a shaft according to the present invention, wherein said shaft is formed from a coextruded shaft having a polyimide/liquid crystal polymer blend surrounding its inner diameter and polyimide surrounding its outer diameter;

FIG. 14 is a cross-sectional view of a shaft according to the present invention, wherein said shaft is formed from a coextruded shaft having a polyimide/liquid crystal polymer blend surrounding its outer diameter and polyimide surrounding its inner diameter;

FIG. 15 is a cross-sectional view of a shaft according to the present invention having an inner layer of polytetrafluoroethylene surrounded by an outer layer comprising thermoplastic polyimide or a thermoplastic polyimide blend;

FIG. 16 is a cross-sectional view of a shaft according to the present invention comprising inner and outer layers of polyimide surrounding an intermediate layer comprising a blend; and FIG. 17 is a partial sectional view of the shaft of a catheter according to the present invention.

DESCRIPTION OF THE PREFERRED EMBODIMENTS

The invention lies in a high strength, thin walled, balloon, and in some instances the catheter shaft or portions thereof, formed from a thermoplastic polyimide. The invention also encompasses the process for manufacturing such a balloon and/or catheter shaft, and could also be utilized in the production and manufacture of guide catheters or infusion catheters.

A balloon of this invention is preferably obtained by extruding thermoplastic polyimide tubing and then expanding the extruded tubing axially and radially. Any conventional extruder may be employed to perform the extrusion process.

Figure 1:
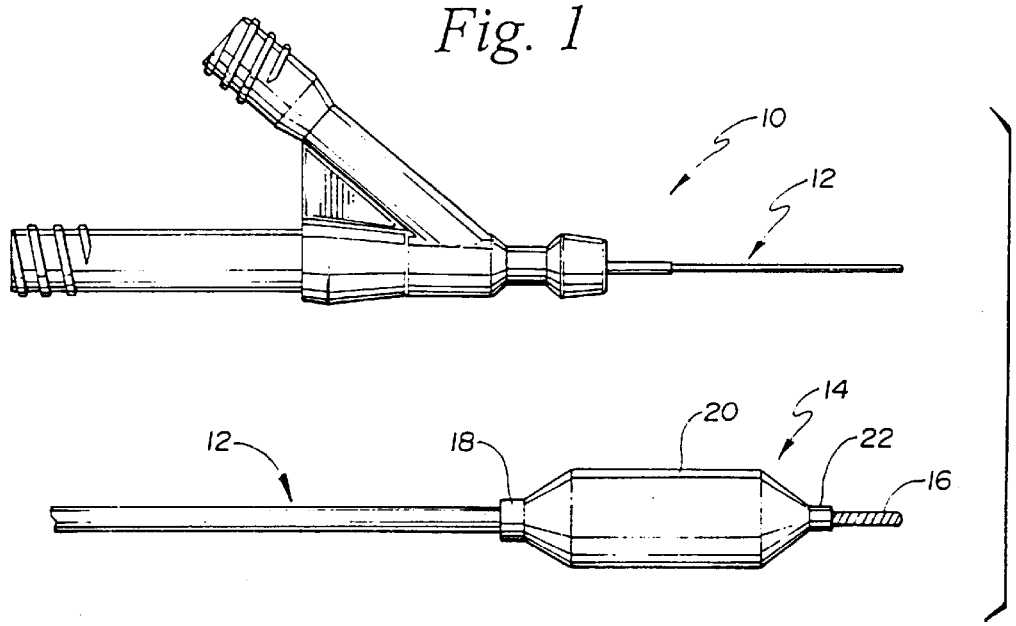
FIG. 1 is a schematic; somewhat idealized view of a balloon catheter using thermoplastic polyimide according to the invention in both shaft and balloon portions.

FIG. 1 shows a schematic view of a balloon catheter, shown generally at 10. Catheter 10 has an elongated flexible shaft 12 which according to the invention, may at least in part, be comprised of thermoplastic polyimide. That is, the entire length thereof may consist of thermoplastic polyimide or a longitudinal section or sections thereof may consist of thermoplastic polyimide or it may be entirely of another material with only the balloon being of thermoplastic polyimide. Since it is thermoplastic at least in part, shaft 12 may be formed by tubular extrusion as is the case of the techniques known in this art for extruding other thermoplastic materials such as the PET aforementioned and as already described hereinabove. In a preferred embodiment of the present invention, thermoplastic polyimide is present in both shaft and balloon portions.

Mounted at the distal end of catheter 10, shown in the lower portion of FIG. 1, which is enlarged to show detail, shaft 12 is fitted with an inflatable thin wall balloon generally designated at 14 (shown inflated). Depending on the particular construction of the catheter, the distal tip 16 may be the distal end of a guide wire as shown or it may be the distal end of the catheter per se.

Shaft 12 has at least one lumen (not shown) extending from its proximal to its distal end. Depending on its construction, multiple lumens may be provided. In any case, at least an inflation lumen extends through shaft 12 for selective inflation and deflation of balloon 14. Any or all of the lumens may be made from thermoplastic polyimide.

Balloon 14 is a thin wall thermoplastic polyimide balloon formed in the art known manner by blow molding as described above. This technique is also discussed in the aforementioned U.S. Pat. No. 4,490,421 for forming PET balloons. As seen in FIG. 1, a balloon in one embodiment comprises a proximal waist portion 18 bonded to the distal end of shaft 12, an intermediate inflatable body portion 20 of a larger diameter than waist 18, and a smaller distal end portion 22.

Thermoplastic polyimide is a linear aromatic polyimide first developed by NASA and described in NASA Conf. Pub. #2334 (1984) at pp. 337–355, entitled THERMOPLASTIC/ MELT-PROCESSABLE POLYIMIDES, authored by T. L. St. Clair and H. D. Burks.

The structural formula is shown as follows:

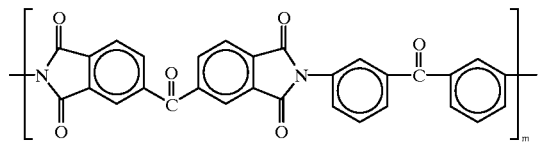

Also shown in that reference is a polyimide sulfone:

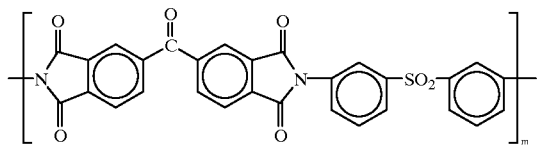

and is a polyphenylene ethersulfideimide:

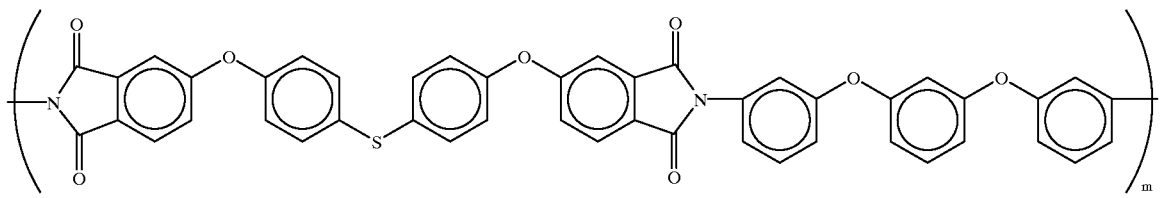

Any of the above examples of polyimides may be used according to this invention.

One such thermoplastic polyimide is available commercially under the tradename AURUM® from Mitsui Toatsu Chemicals, Inc., of Tokyo, Japan. It is the thermoplastic polyimide resin which is described in detail in U.S. Pat. No. 5,069,848 issued Dec. 3, 1991 and European Patent Application 0,391,633 and is shown as having the following structural formula:

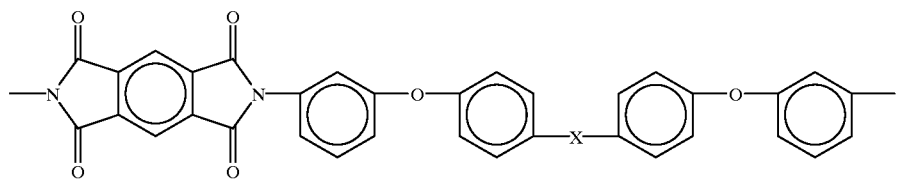

30 wherein X is a single bond or a hexafluoroisopropylidene group, the foregoing references being incorporated herein in their entirety by reference.

Thermoplastic polyimide, as used herein, refers to any polyimide polymer which is reprocessable, i.e., the polymer can be heated to a temperature at which it is soft enough to be reprocessed or extruded but at which temperature it will not decompose to any appreciable degree. Thermoset polyimide, by contrast cannot be reprocessed or reextruded after it has been formed due to the fact that the material crosslinks or forms chemical bonds as the material is being formed.

Applicants have found that the thermoplastic polyimide, when formed into a balloon by stretching and blowing, exhibits amorphous or only slightly crystallized (up to 10%) behavior.

The extruded thermoplastic polyimide tubing for use in making balloons according to this invention can be formed with wall thicknesses as low as on the order of 0.001 to 0.015 inches which can readily be used for forming balloons by blow molding with wall thicknesses on the order of 0.0003" to 0.003" inches.

The present invention has several important advantages. First, thermoplastic polyimide balloons offer thin walls but have a high burst pressure, up to 16 atmospheres and even higher, up to 20 atmospheres. Thermoplastic polyimide shafts are readily extrudable. Thermoplastic polyimide decomposes at a temperature range above about 400°–410° C. The softening temperature of thermoplastic polyimide is about 320°–380° C., and the melting temperature is about 340–410° C. The physical properties of thermoplastic polyimide offer the opportunity of secondary forming operations. For example, the material as extruded tubing can be reheated and a balloon can be blown out of it. Thermoplastic can be remelted. Scrap can be ground up and run through an extruder again. Thermoset polyimide cross links upon curing, which precludes the possibility of remelting for reuse or recycling.

Figure 2:
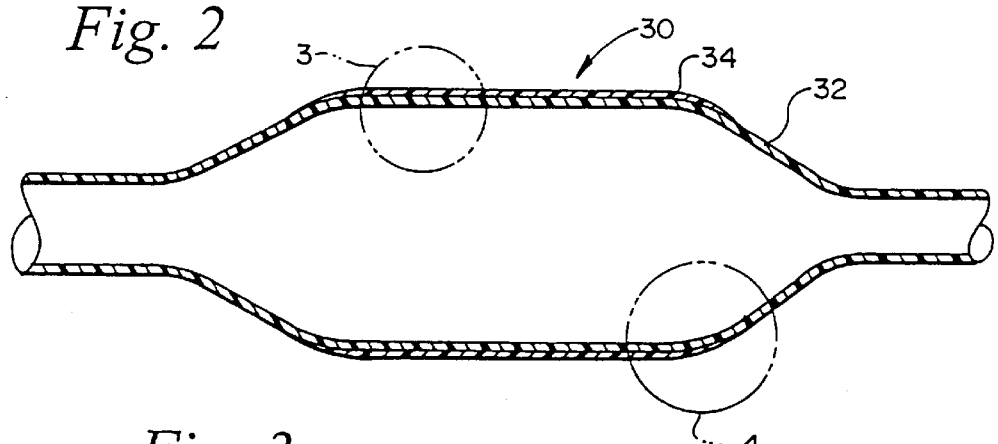
FIG. 2 is a partial sectional view of the distal portion of the catheter shown comprising a longitudinal cross-sectional view of the balloon of FIG. 1.
Figure 3:
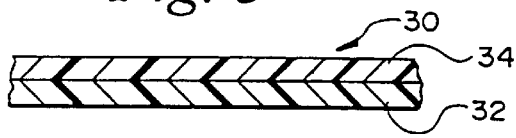
FIGS. 3 and 4 are enlarged cross-sectional views of portions of a wall of a balloon having a plurality of layers forming the wall i.e., a composite of thermoset and thermoplastic polyimide.
Figure 4:
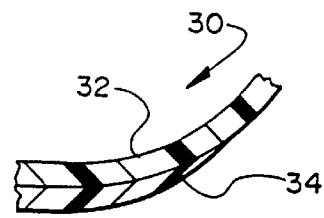

There is a tendency for the fracture mode upon failure of prior art thermoset polyimide balloons to be more of a catastrophic fracture rather than the preferred longitudinal burst mode of thermoplastic polyimide balloons of the invention. For this reason, an alternate embodiment of the invention with respect to balloon construction may comprise a multiple layer balloon of the type shown in FIGS. 2–4. This balloon generally designated 30 is comprised of a blow molded balloon of thermoplastic polyimide having a deposited outer layer 34 of prior art thermoset polyimide, polyamide, or any other material laid down in the known manner on the inflated thermoplastic polyimide 32 of the balloon. Such construction provides a balloon having predominantly longitudinal burst characteristics. This embodiment also offers one the opportunity of tailoring the compliance characteristics of the balloon by selectively altering the number, arrangement and thickness of these layers in a variety of configurations. Moreover, the thermoplastic polyimide balloons of the invention may have no outer layer at all or they may carry a single outer layer or multiple outer layers (fill or partial) of extruded thermoplastic polyimide or other polymer materials for layer 34.

In manufacturing the balloons of the invention, techniques and tools utilized in the prior art for thermoplastic balloons are readily adaptable.

Considering all of the foregoing, thermoplastic polyimide balloons may be readily manufactured which have, for example, diameters of about 1.5–25 mm, lengths of about 5–200 mm, wall thicknesses of about 0.0003–0.003 inches and to any of the typical ranges for balloon dimensions and strengths as typically utilized in the medical industry heretofore. The minimum length is from about 5 mm to about 10 mm, and the most preferred length is about 20 mm in length.

EXTRUSION OF THERMOPLASTIC POLYIMIDE

The drying and extrusion equipment must be thoroughly clean and dry to reduce possibility of material contamination. It is important to sufficiently pre-dry the resin prior to extrusion to prevent creation of surface defects caused by moisture. The resin can be dried by a desiccant type hot air dryer using −40 F. dew point air in a plenum style hopper. The moisture content of the polyimide is controlled to less than 100 ppm by varying both drying temperature and time. Polyimide resin dried at a temperature of 180 C. in excess of 10 hours provides desired moisture levels. An extruder with a length to diameter ratio of about 25:1 and a minimum of three barrel temperature control zones with additional heater control zones for adapter, head and die is adequate. Temperature controllers are proportioning type in order to maintain tight temperature control and a homogeneous melt. Both barrel and screw of the extruder are made of conventional bimetallic material that is surface hardened and chrome plated. Conventional nitride metals tend to degrade by oxidation which causes the generation of black rust at high temperatures. A preferred screw for the extruder is a Barrior design having a length to diameter ratio of from 18 to 28:1 and a compression ratio of 2.7:1 with a zone distribution of about 25% feed, 46% compression, and 30% metering. General purpose screw with 2.5 to 3.5:1 compression ratios and a relatively constant transition from feed to metering zone have also worked effectively. Breaker plate, adapter, head, and tooling are hard chrome plated and streamlined, i.e., gradual transitions, rounded edges and minimal obstructions. Screen packs with a micron rating of 40 to 80 mesh having stainless steel gauge construction are generally sufficient to generate adequate back pressure. Die and tip cross-sectional area drawdown ratios (which is the area defined by the die and mandrel divided by the cross-sectional area of the extruded tubing) can range from 3 to 30:1, and die land lengths range from 10 to 60 times the desired product wall thickness. Sizing can be accomplished by free extrusion methods, maintaining constant nitrogen pressure inside the tubing while being quenched in a conventional water bath at ambient temperatures.

The pre-dried thermoplastic polyimide pellets are preferably delivered to the feed throat of an extruder from a plenum style/hopper, and conveyed forward through several heating zones by rotating the extruder screw. Melt temperature of the polyimide is maintained from 340 C. to 410 C. by the various zone temperature controllers, and by shear generated from the action of a ¾ or 1¼ inch diameter screw rotating at speeds ranging from 2 to 50 RPM. The material then passes through a screen pack, breaker plate, adapter, tooling head, and extrusion tooling where it is shaped to form the desired product. Optimally, the residence time in the extruder is kept to a minimum. Once the material exits the tooling in its desired form, it needs to be cooled. One way to perform the cooling process is to pass the extruded tubing from the extruder, through an air gap between tooling and quench tank ranging from 0.25 to 25 inches, and into a water bath maintained at a temperature ranging from 40 F. to 120 F. A haul-off may be used to pull the tube from the cooled end through the quench tank. Thereafter, the product is spooled or cut to length as desired.

BALLOON FORMING WITH THERMOPLASTIC POLYIMIDE

Some minimal initial orientation of polyimide material is accomplished as the material is drawn down during extrusion. This orientation process is typically known as machine orientation and is formed in the direction of extrusion operation. A small amount of additional longitudinal orientation occurs during balloon formation. This additional orientation is the result of the material elongation at blow molding temperatures, and is caused by the weight of the balloon mold stretching the tubing downward at a ratio of 1.1 to 3:1 at molding temperatures ranging from 230 C. to 330 C. The preferred longitudinal stretch time at molding temperatures is from 8 to 10 minutes. Method improvements to optimize stretching and heating will probably reduce stretch times. Once the optimum longitudinal stretch is achieved, the tubing is expanded radially using internal pressures ranging from 3 to 100 psig. However, the preferred pressure is 20 to 50 psig. This is accomplished by providing a pressurized fluid or gas, preferably nitrogen gas, to the inner lumen of tubing. Tubing extends outside both ends of the mold, one end is clamped off such that no gas can flow through it, and the opposite end is pressurized to form the balloon. An appropriate mold with the tubing inside, may be heated while pressure is applied. The preferred molding temperature ranges from 260 C. to 300 C. The dimensions to which it is stretched are preferably controlled by performing the radial stretching while the tubing is in a mold having the shape of the desired balloon. Suitable molds are known in the art. The tubing subjected to specific interior pressures and exterior heat is held stationary for a period of time, preferably 4 to 6 minutes, while the balloon and waist portions yield completely and stabilize. Method improvements to optimize balloon mold heating will probably result in reduced heat soak cycles. The radial expansion, or hoop ratio (calculated by dividing the inner diameter of the balloon by the inner diameter of the extruded tubing), should be in the range of 3 to 8:1. The preferred hoop ratio is approximately 5:1. The tubing, now comprising the balloon, is next cooled. One way to cool the balloon is to remove the mold from the heat chamber and place it in a cooling bath. The cooling bath is preferably maintained at ambient temperature. The balloon may for example, remain in the cooling bath for approximately 10 seconds. However, a chilled bath can be used to reduce the quench cycle times. Finally, the ends of the tubing extending from the mold are cut off (unless integral catheter shaft/balloon construction is intended) and the balloon is removed from the mold by removing either the distal or proximal end from the body section of the mold, then gently pulling the balloon from the remaining mold sections.

As already indicated, for any given catheter construction, the entire shaft 12 could be polyester, polyethylene, thermoset polyimide or anything else known in the art. The thermoplastic polyimide balloon would be bonded to such a shaft. On the other hand, the balloon may be integral with the shaft or a portion thereof to provide an all thermoplastic polyimide construction.

The shaft may be composed of a blend of materials. The entire shaft or a portion thereof may be coextruded. For example, a shaft may include a layer of polytetrafluoroethylene (PTFE) surrounded by thermoplastic polyimide or a blend of thermoplastic polyimide and other polymeric and/or reinforcement components. Such a blend may comprise PTFE or carbon and thermoplastic polyimide. Examples of such blends includes up to about 10% PTFE or about 15% carbon and a balance of thermoplastic polyimide. Another blend may include liquid crystal polymer, radiopaque materials such as bismuth salts, tungsten or titanium, silver or gold (which would impart conductivity to the blend). A shaft according to the present invention may include inner and outer layers of thermoplastic polyimide surrounding an intermediate layer comprising a blend as described above.

The shaft and/or balloon may be reinforced. The reinforcement material may comprise various types of continuous or intermittent reinforcing components used in the composites of this invention. Among such suitable materials are continuous fiber or filament forms such as polyester, polyamide or carbon fiber, and further may be sphere and particulate forms such as glass. Reinforcing material may comprise glass, carbon, ceramic, fluoropolymer, graphite, liquid crystal polymers, polyester, polyamide, stainless steel, titanium and other metals such as nitinol, or radiopaque materials (such as Bismuth or Tungsten) and the like.

The continuous reinforcement may be used in filamentary form or it may be employed in the form of a yarn or as a fabric of plain weave, satin weave, twill weave, basket weave, braid, winding or the like. The composite structure may comprise parallel aligned continuous filaments extending within or along the inner or outermost dimension of the structure, the fibers being bonded together with the above-described thermoplastic polyimide which intimately contacts substantially the whole of the surfaces of the filaments.

Figure 5:
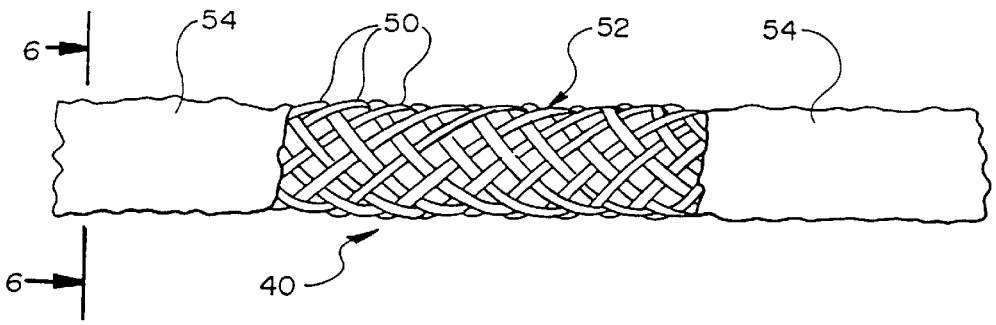
FIG. 5 is a front view, with portions broken away, showing a shaft of the catheter of FIG. 1 which is a polyimide shaft with braided reinforcement.
Figure 6:
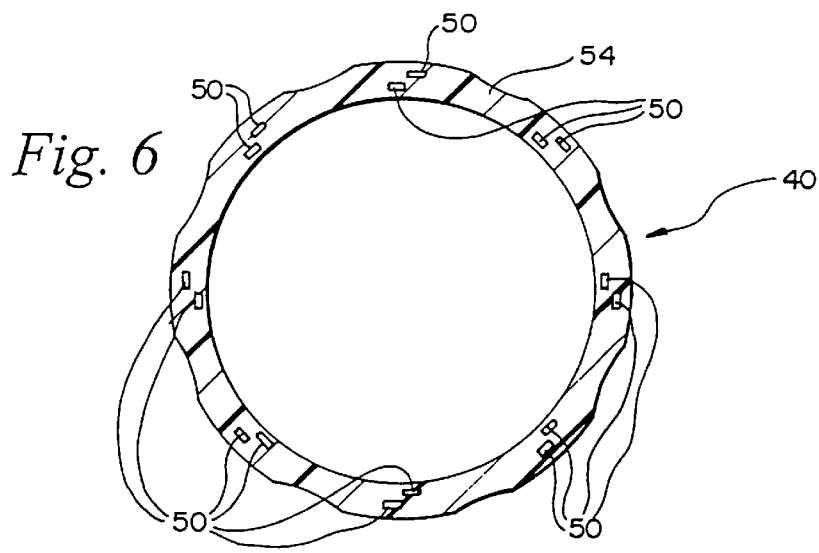
FIG. 6 is a cross-sectional view of the shaft of FIG. 5 taken on line 6—6 of FIG. 5.

FIGS. 5–6 illustrate an alternative embodiment of the shaft, shown generally at 12 of FIG. 5. Shaft 12 has a continuous reinforcement in the form of a tubular braid 52 formed of individual strands 50. Polyimide material 54 encases tubular braid 52 on both the inner and outer surfaces of braid 52. Braid 52 is shown centered in polyimide material 54.

Figure 7A:
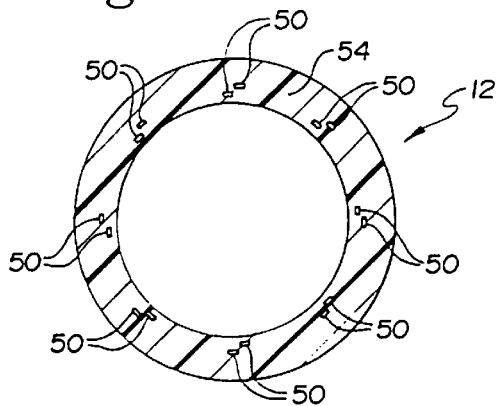
FIG. 7A is a cross-sectional view of a shaft according to the present invention, wherein the shaft has a reinforcement at its innermost diameter and a polyimide coating over the reinforcement structure.
Figure 7B:
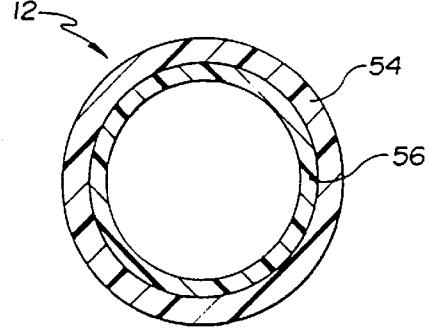
FIG. 7B is a cross-sectional view of a shaft according to the present invention comprising a thermoplastic polyimide material surrounding a reinforcement material.

FIG. 7A illustrates an alternative embodiment of the shaft of the present invention, wherein shaft 12 has a reinforcement at its innermost diameter and a polyimide coating over the reinforcement structure. Although a braided reinforcement is shown, any continuous or intermittent reinforcement as described herein may be employed. For example, FIG. 7B shows a thermoplastic polyimide material 54 surrounding reinforcement material 56 comprising a material such as polyester, polyamide malleable metal or plastic.

FIG. 8 illustrates a further alternative embodiment of the shaft of the present invention, wherein shaft 12 has a reinforcement material 50 embedded near the outermost diameter of thermoplastic polyimide substrate 54. Again, although a braided reinforcement material is shown, any reinforcement as described herein may be employed.

FIG. 9–15 illustrate still further embodiments of the shaft of the present invention. FIG. 9 shows shaft 12 having reinforcement material 50 at the innermost diameter of thermoplastic polyimide material 54. Reinforcement structure 50 is coated by polyimide material 54, but is almost exposed.

FIG. 10 shows a shaft formed from a blend of polyimide and a reinforcing material. The reinforcement material as shown is in discontinuous form, i.e. dispersed particulate such as glass spheres 60 embedded throughout thermoplastic polyimide material 54. Blends as described hereinabove may be employed, as may carbon fibers as also described above.

FIG. 11 shows shaft 12 formed of an inner layer 62 of a fluoropolymer, a layer of polyimide material 54 surrounding inner layer 62 and a reinforcement material 50 as described hereinabove bonded to or embedded in polyimide material 54. FIG. 11 is also an example of a cross section of a guide catheter according to the present invention. By varying diameter, length and flexibility of the shafts described herein, various medical devices including infusion catheters and guide catheters can be produced.

FIG. 12 shows shaft 12 formed of polyimide inner layer 68, intermediate reinforcing material 70 as described hereinabove, and an outer polyimide layer 72. FIG. 13 shows shaft 12 having layer 74 comprising a polyimide/liquid crystal polymer blend layer, surrounded by a layer of polyimide 76. An alternative configuration wherein polyimide/liquid crystal polymer blend layer 74' surrounds polyimide layer 76' is shown at FIG. 14.

Liquid crystal polymers are known to the art. Liquid crystal polymers are rigid, rod-like macromolecules which typically contain a substantial number of polyvalent aromatic groups such as phenylene. After alignment or orientation by shear or elongational forces, the steric hindrance of molecular rotation provided by the polyvalent or other groups causes the liquid crystal polymers to retain their orientation to effect hardening. Examples of liquid crystal polymers are VECTRA sold by Hoechst-Celanese, or HX materials sold by DuPont, XYDAR and Econol (terpolymer of hydroxybenzoic acid, biphenol and terephthalic acid) from Dartco and Sumitomo Chemical, respectively, Vecrora from Polyplastic, and Ueno (terpolymer of 2-oxy-6-naphthoic acid, biphenol, and terephthalic acid) from Ueno Seiyaku, and any other polymer material having a rod like molecule which imparts a tendency to align more readily during melt flow than flexible chain polymers.

The embodiment of shaft 12 shown at FIG. 15 includes an inner layer 80 of polytetrafluoroethylene (PTFE) surrounded by an outer layer 82 of thermoplastic polyimide. Outer layer 82 may alternatively be comprised of a blend of thermoplastic polyimide and other components as described hereinabove. A still further embodiment of shaft 12 according to the present invention as shown at FIG. 16 may include inner and outer layers 86,88 of thermoplastic polyimide surrounding an intermediate layer 90 comprising a blend as described above.

A still further embodiment of shaft 12 is shown at FIG. 17, where a wire winding type reinforcing material 92 is used within the polyimide to reinforce polyimide material 54.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This invention has been carefully described herein in order to provide those skilled in the art with the information necessary to perform the requisite process and obtain the desired product. However, it is to be understood that the invention can be carried out by different techniques and a variety of equipment. Therefore, various known modifications, both as to equipment details and operating procedures, may be incorporated without departing from the scope of the invention itself.

This completes the description of the preferred and alternate embodiments of the invention. Those skilled in the art may recognize other equivalents to the specific embodiment described herein which equivalents are intended to be encompassed by the claims attached hereto.

What is claimed is:

1. An improved balloon catheter comprising a shaft portion having a proximal end and a distal end, and a balloon portion located at the distal end of said shaft portion, wherein the improvement comprises said shaft portion of the balloon catheter being comprised of thermoplastic polyimide having a melting point in the range of about 340° C.–410° C.

2. The balloon catheter of claim 1 in which the balloon is comprised at least in part of thermoplastic polyimide.

3. An improved balloon catheter comprising a shaft portion having a proximal end and a distal end, and a balloon portion located at the distal end of said shaft portion, wherein the improvement comprises at least a portion of the shaft being comprised of thermoplastic polyimide having a melting point in the range of about 340° C. to about 410° C. coextruded with another material.

4. An improved balloon catheter comprising a shaft portion having a proximal end and a distal end, and a balloon portion located at the distal end of said shaft portion, wherein the improvement comprises the balloon portion being comprised of an innermost balloon layer and at least one additional layer, and wherein at least two of said layers are comprised of polyimide, and one of said polyimide layers is comprised of thermoplastic polyimide.

5. The balloon catheter of claim 4 in which the inner most balloon layer is thermoplastic polyimide.

6. A balloon catheter, said balloon catheter having a shaft comprised at least in part of thermoplastic polyimide having a melting point between about 340° C.–410° C., the balloon portion being comprised of multiple layers, one of said layers being an innermost layer, wherein at least one of said layers is thermoplastic polyimide.

7. A balloon catheter, said balloon catheter having a shaft comprised at least in part of thermoplastic polyimide having a melting point between about 340° C.–410° C., the balloon portion being comprised of multiple layers, one of said layers being an innermost layer, wherein one of said layers is thermoplastic polyimide, and the other said layer is thermoset polyimide.

8. The balloon portion of claim 7 wherein the innermost layer is thermoplastic polyimide.

9. A catheter shaft comprised at least in part of thermoplastic polyimide having a melting point in the range of 340° C.–410° C., said shaft further comprising a reinforcement material.

10. A catheter shaft comprised at least in part of thermoplastic polyimide, said shaft further comprising a reinforcement material, and wherein said reinforcement material is a fiber.

11. A catheter shaft comprised at least in part of thermoplastic polyimide, said shaft having an inner diameter covered with a fluoropolymer, said shaft further comprising a reinforcement material in the polyimide material.

* * * * *